United States Patent [19]
Wagner et al.

[11] Patent Number: 5,108,914
[45] Date of Patent: Apr. 28, 1992

[54] PROCESS FOR THE SYNTHESIS OF L-ALPHA-AMINO ACIDS

[75] Inventors: Fritz Wagner, Braunschweig; Christoph Syldalk, Hildesheim; Vera Mackowiak; Karsten Krohn, both of Braunschweig; Hartmut Höke, Castrop-Rauxel; Albrecht Läufer, Essen, all of Fed. Rep. of Germany

[73] Assignee: Rütgerswerke Aktiengesellschaft, Frankfurt, Fed. Rep. of Germany

[21] Appl. No.: 452,440

[22] Filed: Dec. 19, 1989

[30] Foreign Application Priority Data

Jan. 2, 1989 [DE] Fed. Rep. of Germany ....... 3900007

[51] Int. Cl.$^5$ ............... C12P 13/04; C12P 13/12; C07C 149/247; C07C 101/08
[52] U.S. Cl. .................... 435/106; 435/108; 435/113
[58] Field of Search ............ 435/108, 113, 106

[56] References Cited

U.S. PATENT DOCUMENTS 4,211,840 7/1980 Nakamori et al. ............ 435/108
4,248,967 2/1981 Viglia et al. ................. 435/106

FOREIGN PATENT DOCUMENTS 0158866 10/1985 European Pat. Off. .
0309310  3/1989 European Pat. Off. .
2811303  9/1978 Fed. Rep. of Germany .
3712539C2 2/1988 Fed. Rep. of Germany .
2393848  1/1979 France .

Primary Examiner—Herbert J. Lilling
Attorney, Agent, or Firm—Armstrong, Nikaido, Marmelstein, Kubovcik & Murray

[57] ABSTRACT

Microorganisms with the ability to cleave enantioselectively 5-substituted hydantoins to L-alpha-amino acids are cultivated in a known manner in a batch preparation. By one-time dosage of a nondegradable enzyme inductor of the structure

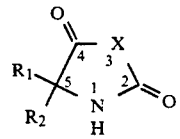

(where $R_1$, $R_2$ and X are specifically defined) an increased enzyme activity combined with an increased reaction rate is achieved.

8 Claims, No Drawings

PROCESS FOR THE SYNTHESIS OF L-ALPHA-AMINO ACIDS

BACKGROUND OF THE INVENTION

The invention relates to a new microbial-enzymatic process for the synthesis of L-alpha-amino acids from 5-substituted hydantoins.

L-Alpha-amino acids are used as an additive for foods and nutrients as well as for the manufacture of pharmaceutical products and as an intermediate product for chemical syntheses.

According to West German Patent DE 3,712,539 C2, L-alpha-amino acids can be obtained from 5-substituted hydantoins or N-carbamoyl-alpha-amino acids by biochemical conversion by means of microorganisms. Optimization tests with the strains described in this patent specification have shown that the growth and the enzymatic synthesis is favorably influenced by addition of glucose and ammonium sulfate and yeast extract to the medium. However, the imparting of a high specific enzyme activity is linked to the presence of a suitable inductor and of manganese ions in the medium, since only under the influence of a suitable inductor do the organisms begin to form the enzymes participating in the conversion, such as hydantoin racemase, hydantoinase and L-N-carbamoylase. According to West German Patent DE 3,712,539 C2, D,L-3'-methyleneindolyl-5-hydantoin can function both as an inductor and as a carbon source.

However, it is therefore not sufficient to add this inductor in a batch preparation to the medium at the beginning, since its effect decreases with time. Only fresh addition leads again to an increase of the activity. Dosage of the inductor in the later growth phase over 4 to 5 hours has also proved successful; nevertheless, this means an undesirably high inductor consumption. Moreover, products are formed that have an inhibiting effect on the growth and visibly color the medium. For isolation of the formed L-alpha-amino acid, these degradation products must additionally be removed, which causes an increased purification expense.

It is a further disadvantage that, for this inductor, an organic solvent such as, for example, polyethylene glycol, must be employed in the culture medium.

The object of the present invention is therefore to improve the known process for the synthesis of L-alpha-amino acids by providing an inductor which as far as possible is not degraded during the microbial conversion, which forms no products inhibiting the growth and the enzyme activity, which necessitates no additional purification expense in the working-up of the reaction mixture and which permits a high yield of L-alpha-amino acids even without additional solvents.

SUMMARY OF THE INVENTION

According to the present invention, it has been found that compounds with the structure

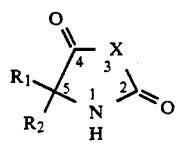

where
$R_1$ and $R_2$ are the same or different,
$R_1 = H$ or an alkyl group with 1–4 C atoms,
$R_2 =$ an alkyl group with 1 to 4 C atoms or the following residues

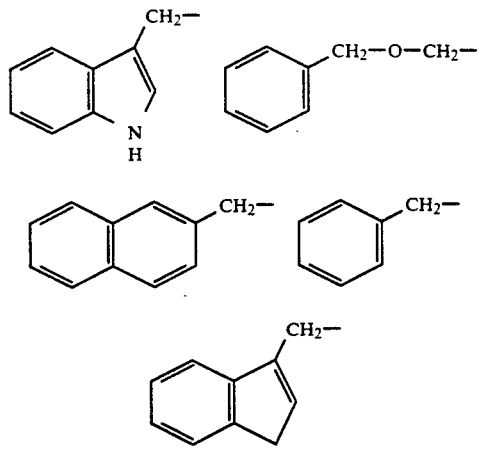

and $X = >N\text{-Alk}$ or $>CH\text{-Alk}$ or $>CH_2$,
where Alk represents a branched or unbranched alkyl chain with 1–4 C atoms,
can be employed as highly effective inductors in the known process for the synthesis of L-alpha-amino acids from 5-substituted hydantoins or N-carbamoyl-alpha-amino acids by biochemical conversion by means of microorganisms.

Unexpectedly, the inductors of the process of the present invention are not markedly degraded despite their good induction effect during cultivation. Growth inhibition due to accumulation of degradation products does not occur, and thus the demand for inductor is substantially reduced. Furthermore, by virtue of the inductor according to the invention, there is achieved a process simplification, since the inductor is added as an initial charge one time at the beginning or in the course of cultivation of the biomass and its activity persists until the end. Notwithstanding, a higher enzyme activity can simultaneously be observed.

DESCRIPTION OF PREFERRED EMBODIMENTS

In Table 1, the influences of the inductors of D,L-3'-methyleneindolyl-5-hydantoin and 3-N-methyl-D,L-3'-methyleneindolyl-5-hydantoin are compared with each other.

TABLE 1

| Growth and enzyme induction with coryneform bacteria DSM 3747 after 16 hr in the 20-liter bioreactor | | | |
|---|---|---|---|
| Inductor in initial charge | | 1.0 g/liter D,L-5-IMH | 1.0 g/liter 3-N—CH$_3$-D,L-5-IMH |
| X (g/liter) | | 14 | 15 |
| Y$_{x/s}$ | | 0.35 | 0.40 |
| μ (hr$^{-1}$) | | 0.22 | 0.27 |
| Specific | Trp | 0.047 | 0.230 |
| activity | cTrp | 0.035 | 0.037 |
| (mmol/g BDM · hr) | Trp + Ctrp | 0.082 | 0.267 |

Trp = L-tryptophan
CTrp = N-carbamoyl-D,L-tryptophan
X = biological dry mass (g/liter)
$Y_{x/s}$ = yield coefficient = $\frac{X\ (g/liter)}{substrate\ (g/liter)}$
μ = specific growth rate (liter/hr)
D,L-5-IMH = D,L-3'-methyleneindolyl-5-hydantoin
3-N—CH$_3$-D,L-5-IMH = 3-N-methyl-D,L-3'-methyleneindolyl-5-hydantoin Cultivation was carried out in the bioreactor in the mineral salt medium with initial charge of glucose and addition of glucose over 16 hours according to Example 1.

The enzyme activities were measured after various cultivation times according to Example 2. In comparison with D,L-3'-methyleneindolyl-5-hydantoin-induced cells, 3-N-methyl-D,L-3'-methyleneindolyl-5-hydantoin-induced cells exhibited approximately 5 times higher specific activity.

With a one-time initial charge of 1.0 g/liter of 3-N-methyl-D,L-3'-methyleneindolyl-5-hydantoin in the nutrient medium, and with a biological dry mass (BDM) of 29 g/liter, a specific activity of 0.352 (mmol/g BDM.hr) of Trp, 0.039 (mmol/g BDM.hr) of CTrp and 0.391 (mmol/g BDM.hr) of Trp+CTrp can be obtained in 29 hr.

The concentration of this new inductor remains constant throughout the entire period. In contrast, with D,L-3'-methyleneindolyl-5-hydantoin as inductor, specific activities of only 0.107 (mmol/g BDM.hr) of Trp, 0.025 (mmol/g BDM.hr) of CTrp and 0.132 (mmol/g BDM.hr) of Trp+CTrp can be achieved.

With 3-N-methyl-D,L-3'-methyleneindolyl-5-hydantoin as the inductor, a 3 to 5 times higher enzyme activity is achieved and the product ratio is clearly shifted in favor of tryptophan formation. Inductors that can be employed according to the invention are compounds of the general structure

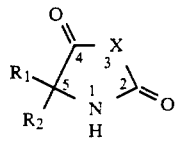

where
$R_1$ and $R_2$ are the same or different,
$R_1$ = H or an alkyl group with 1–4 C atoms,
$R_2$ = an alkyl group with 1 to 4 C atoms or the following residues

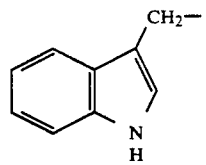

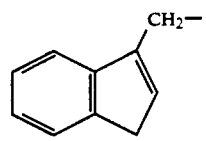

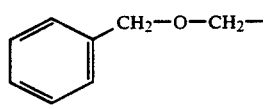

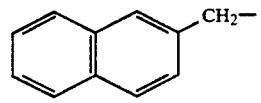

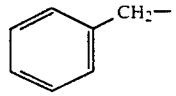

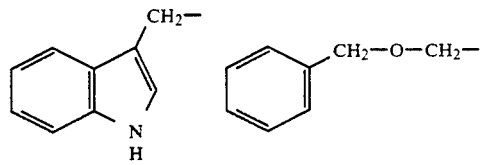

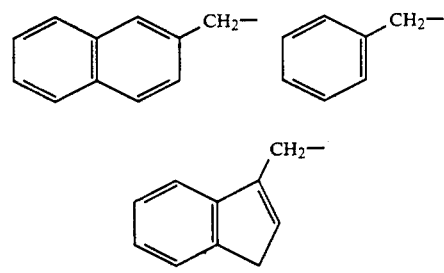

and X = >N-Alk or >CH-Alk or >$CH_2$, where Alk represents a branched or unbranched alkyl chain with 1–4 C atoms.

Accordingly, the inductors according to the present invention are hydantoins or diketopyrrolidines, which are substituted both in the 3-position and in the 5-position. Possible substituents in the 3-position are lower alkyl groups such as, for example, the methyl, ethyl, n-propyl, i-propyl, n-butyl, i-butyl and tert-butyl groups. The 5-position can be monosubstituted or disubstituted, and the substituents $R_1$ and $R_2$ are the same lower alkyl groups such as the methyl, ethyl, n-propyl, i-propyl, n-butyl, i-butyl and tert-butyl groups, or $R_1$ is hydrogen or a lower alkyl group and $R_2$ is a lower alkyl group or a group of the following structure:

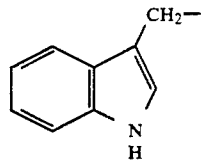

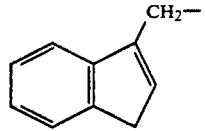

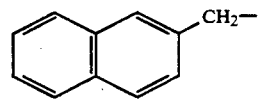

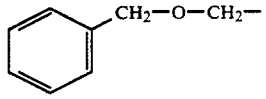

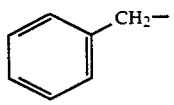

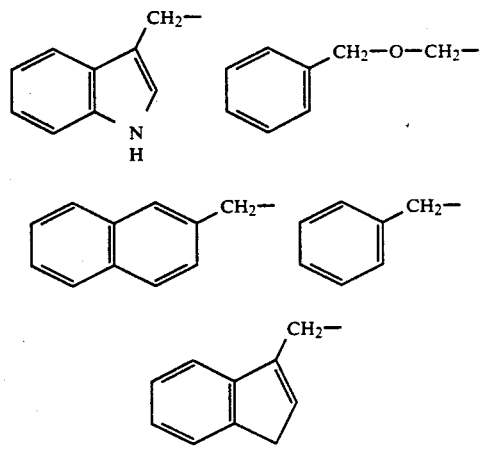

Preferred inductors are hydantoins alkylated in the 3-position with an aralkyl residue in the 5-position. These inductors are added to the culture medium one time in an amount of 0.1 to 2.0 g/liter, right at the beginning or in the course of cultivation of the microorganisms.

The cultivation of the microorganisms and the biochemical hydantoin cleavage occur in a manner known in itself, such as described in, for example, West German Patent DE 3,712,539 C2, the disclosure of which is incorporated herein by reference.

The microorganisms may be prepared as follows: Each time 50 ml of a synthetic nutrient medium with 3-methyleneindolyl-5-hydantoin as the single carbon source of the composition (g/l)

| | |
|---|---|
| $KH_2PO_4$ | 3.0 |
| $(NH_4)_2SO_4$ | 1.0 |
| $MgSO_4.7H_2O$ | 0.2 |
| $FeSO_4.7H_2O$ | 0.01 |
| $CaCl_2.2H_2O$ | 0.01 |
| $MnSO_4.7H_2O$ | 0.00045 |
| D,L-3-methyleneindolyl-5-hydantoin | 1.0 |
| Vitamin solution (Schlegel, Allgemeine Mikrobiologie, Georg Thieme Verlag, Stuttgart, 1976) | 2.0 ml/liter | are mixed with 0.2 to 0.6 g of soil or water samples from various sites and are incubated in a 50 ml Erlenmeyer flasks at 27° C., pH=7.0 and 100 rpm on a rotary agitator for 3 to 5 days. Following 10-fold hetero-inoculation of the 3 to 5 day-old suspensions cultures into fresh, sterile nutrient solutions, the 11th culture suspension is hetero-inoculated on a synthetic nutrient medium solidified with 30 g/l agar-agar and the individual colonies are turned into pure cultures.

To verify the enzyme activity, the microorganisms so prepared first are cultivated in 200 ml of shake cultures at pH=7.0 and 27° C. in a complex medium of the following composition (g/l):

| | |
|---|---|
| fructose | 5.6 |
| yeast extract | 6.5 |
| $(NH_4)_2SO_4$ | 3.9 |
| $K_2HPO_4.3H_2O$ | 2.0 |
| $KHPO_4$ | 0.95 |
| tripotassium citrate | 0.29 |
| $MgSO_4.7H_2O$ | 0.2 |
| $CaCl_2.2H_2O$ | 0.02 |
| $MnSO_4.H_2O$ | 0.01 |
| D,L-3-methyleneindolyl-5-hydantoin | 0.25 |

The cell mass is centrifuged off after 24 h and washed in 0.9% cooking salt solution and centrifuged off again.

The enzyme activity of the cell masses so obtained is tested under the following conditions of reaction: 0.5 g of moist cell mass; 0.25 g of 5-substituted hydantoin or N-carbamoyl alpha amino acids are suspended in 25 ml of 0.1 m phosphate buffer, pH=8.0, and incubated for 24 h at 27° C. Thereupon the cells are centrifuged off, and the supernatant reaction products are analyzed by thin-film chromatography and high-pressure liquid chromatography.

Three cell lines so obtained were filed with the DEUTSCHEN SAMMLUNG FUER MIKROORGANISMEN (DSM) AT Göttingen as

DSM 3745 (CW 3)
DSM 3746 (CW 4)
DSM 3747 (CW 5).

The method of the invention shall be preferably carried out at 20° to 50° C. and a pH between 6.5 and 10. The bacteria, or mutants and enzyme extracts derived from them, of these microorganisms may be used in the free or immobilized state in said method.

Illustratively the enzyme extracts are prepared as follows: a 30% by weight cell suspension in tris buffer is decomposed twice using a Dyno mill in a decomposition vessel of 640 ml with glass beads 0.3 mm in diameter of 3,000 rpm and a flow of 3 liters/h. Following centrifuging of the cell debris, the three enzymes hydantoinase, racemase and L-N-carbamoyl alpha amino acid amidohydrolase are dissolved in the supernatant. This supernatant can be used directly as the crude extract in the method of the invention.

In the process according to the invention, all microorganisms can be employed that cleave substituted hydantoins in the desired manner, preferably such that cleave the hydantoins enantioselectively to the corresponding L-form. This cleavage is also known even in microorganisms of the genera Arthrobacter, Flavobacterium and Pseudomonas.

All 5-substituted hydantoins that are accessible via conversions that are known in themselves are accessible to the process according to the invention.

Examples of 5-substituted hydantoins that can be hydrolyzed with the microorganisms according to the invention through N-carbamoyl-alpha-amino acids to L-alpha-amino acids are listed in Table 2. However, the invention is not limited to these examples.

TABLE 2

| 5-Substituted hydantoins and degradation products | | | | |
|---|---|---|---|---|
| | N-Carbamoyl-amino acid | | Alpha-amino acid | |
| 5-Substituent | % D* | % L* | % D* | % L* |
| Ethylene-2'-methylthio ether | 100 | 0 | 0 | 100 |
| Benzyl | 50 | 50 | 0 | 100 |
| p-Hydroxybenzyl | 56 | 44 | 0 | 100 |
| 3,4-Dihydroxybenzyl | 58 | 42 | 0 | 100 |

TABLE 2-continued

| | 5-Substituted hydantoins and degradation products | | | |
|---|---|---|---|---|
| | N-Carbamoyl-amino acid | | Alpha-amino acid | |
| 5-Substituent | % D* | % L* | % D* | % L* |
| Benzylmethylene ether | 50 | 50 | 0 | 100 |
| 3'-Methyleneindole | 6 | 94 | 0 | 100 |

*configuration

Examples of N-carbamoyl-alpha-amino acids that can be cleaved to L-alpha-amino acids with the microorganisms employed according to the invention are listed in Table 3.

TABLE 3

| Substrate | Product |
|---|---|
| N-Carbamoyl-D,L-tryptophan | L-Tryptophan |
| N-Carbamoyl-L-tryptophan | L-Tryptophan |
| N-Carbamoyl-D,L-phenylalanine | L-Phenylalanine |
| N-Carbamoyl-D-phenylalanine | L-Phenylalanine |
| N-Carbamoyl-D-methionine | L-Methionine |

EXAMPLES

Example 1

Cultivation Conditions

According to West German Patent DE 3,712,539 C2, a preculture of the organisms of the deposited strain (DSM 3747) is prepared. For the main culture, the following conditions are provided:

| | |
|---|---|
| Glucose initial charge | 20 g/liter |
| Glucose dosage | 3–5 g/liter · hr$^{-1}$ starting from the 10th hour |
| Technical yeast extract | 1.0 g/liter |
| $KH_2PO_4$ | 3.4 g/liter |
| $Na_2HPO_4.2H_2O$ | 4.41 g/liter |
| Citric acid monohydrate | 0.64 g/liter |
| $MgSO_4.7H_2O$ | 0.40 g/liter |
| $CaCl_2.2H_2O$ | 0.04 g/liter |
| $FeSO_4.7H_2O$ | 0.04 g/liter |
| $MnCl_2.4H_2O$ | 0.04 g/liter |
| $(NH_4)_2SO_4$ | 6.5 g/liter |
| Inductor* | 1.0 g/liter |
| pH | 7.0 by $NH_3$ titraton (10% aqueous solution) |
| Temperature | 30° C. |
| Cultivation duration | 15 to 30 hr |
| *(a) D,L-5-IMH | 1.0 g/liter (initial charge) + dosage (depending on the cultivation duration) |
| (b) 3-N-$CH_3$—D,L-5-IMH | 1.0 g/liter (new inductor) |

Example 2

Enzyme Activity Test

Samples are taken at specified cultivation times and centrifuged.

100 mg of biological wet mass is suspended in closed 10-ml shaking bottles in 5 ml of 0.1M glycine buffer or 0.05M phosphate buffer (pH 8.5) and shaken with 5 mg of D,L-5-IMH at 27° C. for 2 hours under $N_2$ atmosphere.

The concentration of IMH, N-carbamoyltryptophan and L-tryptophan is determined from the supernatant by HPLC (RP-8 column, Serva, Heidelberg; 50 mM $KH_2PO_4$/25% methanol as mobile phase as well as UV detection at 280 nm; flowrate 1.0 ml/min).

The retention times are:
Trp: 6.1 min
CTrp: 8.5 min
IMH: 16.7 min

Example 3

The biocatalyst is drawn according to Example 1 together with the respective inductors and centrifuged off after 20 hr.

120 g of biological wet mass is stirred into 2 liters of carbonate buffer (0.1 m, pH 8.5, controlled) and 20.0 g (87.2 mmol) of D,L-5-IMH as substrate at 50° C. after one-time $N_2$ gas injection.

a) D,L-5-IMH-induced cells completely convert D,L-5-IMH after 3 hr. In the meantime, CTrp is clearly formed over 2 hr as the reaction product, i.e., no complete conversion occurs, since in the 2nd reaction step the L-N-carbamoylase exerts a limiting effect (Table 4).

b) 3-N-$CH_3$-D,L-5-IMH-induced cells convert D,L-5-IMH within 1 hr. The second reaction step with L-N-carbamoylase proceeds much more rapidly (Table 4).

TABLE 4

Concentrations of intermediate product (CTrp) and product (L-Trp) as well as yields (% L-Trp) after induction with D,L-5-IMH or 3-N-$CH_3$—D,L-5-IMH and conversion with D,L-5-IMH as substrate in the small reactor

| Reaction time (HR) | D,L-5-IMH | | | 3-N-$CH_3$—D,L-5-IMH | | |
|---|---|---|---|---|---|---|
| | CTrp (mmol) | Trp (mmol) | % Trp | CTrp (mmol) | Trp (mmol) | % Trp |
| 0 | 0 | 0 | 0 | 0 | 0 | 0 |
| 1.0 | 14.1 | 56.3 | 64 | <1 | >86 | >99 |
| 1.5 | 11.1 | 74.4 | 85 | <1 | >86 | >99 |
| 2.0 | 8.0 | 81.4 | 93 | | | |
| 3.0 | 3.2 | 82.4 | 94 | | | |

What is claimed is:

1. A process for the synthesis of a L-α-amino acid comprising the steps of
providing a culture medium and a microorganism capable of cleaving a 5-substituted hydantoin,
adding to the culture medium an enzyme inductor which is different than said 5-substituted hydantoin and has the structure

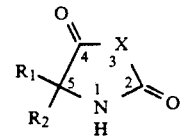

where $R_1$ and $R_2$ are the same or different and $R_1$ is H or alkyl of 1–4 C atoms and $R_2$ is alkyl of 1–4 C atoms or one of the following residues

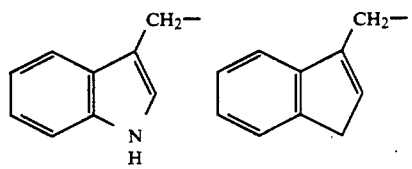

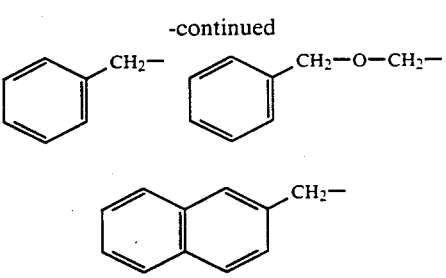

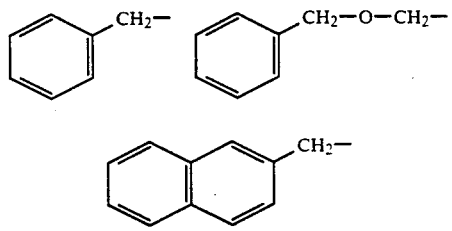

and X is >N-Alk or >CH-Alk or >CH₂, where Alk is branched or unbranched alkyl of 1–4 C atoms, culturing the microorganisms, whereby enzymes are produced without degrading the enzyme inductor, and hydrolyzing a 5-substituted hydantoin with the microorganisms and enzymes.

2. In a process for the synthesis of a L-α-amino acid wherein a culture medium and a microorganism capable of cleaving a 5-substituted hydantoin is provided, an enzyme inductor is added to the culture medium, the microorganism is cultured, whereby enzymes are produced, and a 5-substituted hydantoin is hydrolyzed with the microorganisms and enzymes, the improvement comprising using an enzyme inductor which is different than said 5-substituted hydantoin and which is not degraded during the culturing and having the structure

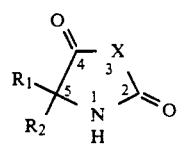

where R₁ and R₂ are the same or different and R₁ is H or alkyl of 1–4 C atoms and R₂ is alkyl of 1–4 C atoms or one of the following residues

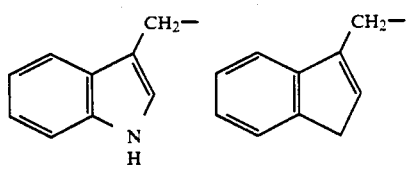

and X is >N-Alk or >CH-Alk or >CH₂, where Alk is branched or unbranched alkyl of 1–4 C atoms.

3. A process according to claim 1, wherein a compound of the structure

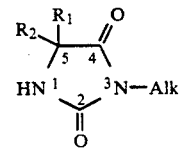

is employed as the inductor.

4. A process according to claim 1 or 3, wherein 3-N-methyl-D,L-3'-methyleneindolyl-5-hydantoin is employed as the inductor.

5. A process according to claim 1 or 3, wherein the inductor is added only one time for the cultivation of the microorganisms.

6. A process according to claim 2, wherein a compound of the structure

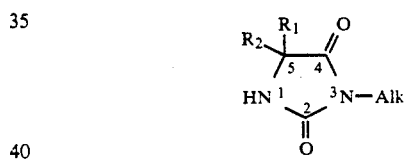

is employed as the inductor.

7. A process according to claim 2 or 6, wherein 3-N-methyl-D,L-3'-methyleneindolyl-5-hydantoin is employed as the inductor.

8. A process according to claim 2 or 6, wherein the inductor is added only one time for the cultivation of the microorganisms.

* * * * *

UNITED STATES PATENT AND TRADEMARK OFFICE
CERTIFICATE OF CORRECTION

PATENT NO. : 5,108,914
DATED : April 28, 1992
INVENTOR(S) : Fritz WAGNER et al

It is certified that error appears in the above-identified patent and that said Letters Patent is hereby corrected as shown below:

On the cover page, Item [75], second line, "Syldalk" should read -- Syldatk --.

Item [57], line 4, "anondegradable" should read -- a nondegradable --.

Signed and Sealed this

Twentieth Day of July, 1993

Attest:

MICHAEL K. KIRK

*Attesting Officer*  *Acting Commissioner of Patents and Trademarks*